United States Patent
Mukoh et al.

(10) Patent No.: US 9,759,545 B2
(45) Date of Patent: Sep. 12, 2017

(54) OPTICAL TOMOGRAPH AND OPTICAL TOMOGRAPHIC METHOD

(71) Applicant: HITACHI-LG DATA STORAGE, INC., Tokyo (JP)

(72) Inventors: Masaki Mukoh, Tokyo (JP); Kentaro Osawa, Tokyo (JP); Tatsuro Ide, Tokyo (JP)

(73) Assignee: HITACHI-LG DATA STORAGE, INC., Tokyo (JP)

( * ) Notice: Subject to any disclaimer, the term of this patent is extended or adjusted under 35 U.S.C. 154(b) by 149 days.

(21) Appl. No.: 14/083,636

(22) Filed: Nov. 19, 2013

(65) Prior Publication Data

US 2014/0204389 A1   Jul. 24, 2014

(30) Foreign Application Priority Data

Jan. 24, 2013 (JP) .................. 2013-011296

(51) Int. Cl.
*G01B 9/02* (2006.01)
*A61B 3/10* (2006.01)

(52) U.S. Cl.
CPC ..... *G01B 9/02091* (2013.01); *G01B 9/02007* (2013.01); *G01B 9/02081* (2013.01); *A61B 3/102* (2013.01); *G01B 2290/70* (2013.01)

(58) Field of Classification Search
CPC ............ G01B 9/02004; G01B 2290/45; G01B 9/02027; G01B 9/02069; G01B 9/02083;
(Continued)

(56) References Cited

U.S. PATENT DOCUMENTS 5,392,116 A   2/1995   Makosch
5,975,697 A * 11/1999  Podoleanu ............. A61B 3/102
                                                                351/206

(Continued)

FOREIGN PATENT DOCUMENTS

CN   102846306 A   1/2013
JP   H06-82313 A   3/1994
(Continued)

OTHER PUBLICATIONS https://en.wikipedia.org/wiki/Bragg%27s_law.*
(Continued)

*Primary Examiner* — Tarifur Chowdhury
*Assistant Examiner* — Mohamed K Amara
(74) *Attorney, Agent, or Firm* — Baker Botts L.L.P.

(57) ABSTRACT

A luminous flux including laser light of different wavelengths outgoing from a light source unit is split into two luminous fluxes, the first luminous flux is focused on a sample with an objective lens, and the second luminous flux functions as reference light without radiating it onto the sample. Signal light reflected from the sample and the reference light are multiplexed by a polarized beam splitter and are made to interfere on four photodetectors out of phase in a photodetection unit. A signal processing unit acquires the optical axis distribution of an object in the sample by using the outputs of the plural photodetectors for every input wavelength, acquiring a detection signal and calculating the ratio of intensities of the detection signals at the different input wavelengths for every position in the sample.

13 Claims, 13 Drawing Sheets

(58) Field of Classification Search
CPC ............ G01B 2290/65; G01B 11/2441; G01B 9/02091; G01B 9/02007; G01B 2290/70; G01B 9/02057; G01B 9/02063; G01B 2290/35
USPC ....... 356/497, 479, 511, 477, 456, 450, 451, 356/478, 495, 503, 484, 609; 351/246, 351/221, 210; 250/227.27, 227.19, 250/559.49, 227.12; 600/425
See application file for complete search history.

(56) References Cited

U.S. PATENT DOCUMENTS

| | | | | |
|---|---|---|---|---|
| 6,002,480 | A * | 12/1999 | Izatt | G01J 3/4412 356/479 |
| 6,006,128 | A * | 12/1999 | Izatt | A61B 5/0066 600/476 |
| 6,242,754 | B1 | 6/2001 | Shiraishi | |
| 6,377,349 | B1 | 4/2002 | Fercher | |
| 6,485,413 | B1 * | 11/2002 | Boppart | A61B 1/00096 356/450 |
| 7,193,766 | B2 * | 3/2007 | Bloom | G02B 26/0841 324/76.36 |
| 7,310,150 | B2 * | 12/2007 | Guillermo | G01N 21/4795 356/479 |
| 7,450,242 | B2 * | 11/2008 | Toida | A61B 5/0066 356/479 |
| 7,544,162 | B2 * | 6/2009 | Ohkubo | A61B 5/0066 385/117 |
| 7,633,623 | B2 * | 12/2009 | Hatori | A61B 5/0066 356/450 |
| 7,903,256 | B2 * | 3/2011 | Sarunic et al. | 356/497 |
| 7,920,271 | B2 * | 4/2011 | Vakoc et al. | 356/479 |
| 8,226,233 | B2 * | 7/2012 | Sugita | A61B 3/102 351/205 |
| 8,390,818 | B2 * | 3/2013 | Hirose | A61B 3/102 356/497 |
| 8,425,036 | B2 * | 4/2013 | Yoshida | A61B 3/102 351/205 |
| 2004/0239938 | A1 * | 12/2004 | Izatt | 356/450 |
| 2004/0239943 | A1 * | 12/2004 | Izatt et al. | 356/479 |
| 2004/0254474 | A1 * | 12/2004 | Seibel | A61B 5/0062 600/473 |
| 2005/0286055 | A1 | 12/2005 | Wang | |
| 2008/0007734 | A1 * | 1/2008 | Park | A61B 5/0066 356/495 |
| 2008/0165366 | A1 | 7/2008 | Schmitt | |
| 2008/0212103 | A1 * | 9/2008 | Walmsley | G04F 13/02 356/450 |
| 2008/0281154 | A1 | 11/2008 | Gono et al. | |
| 2009/0027689 | A1 * | 1/2009 | Yun et al. | 356/511 |
| 2011/0205548 | A1 * | 8/2011 | Sugita | A61B 3/102 356/496 |
| 2011/0228223 | A1 | 9/2011 | Jiao et al. | |
| 2012/0092677 | A1 | 4/2012 | Suehira et al. | |
| 2013/0003015 | A1 * | 1/2013 | Kurosaka | A61B 5/0066 351/206 |
| 2013/0329188 | A1 * | 12/2013 | Buckland | A61B 3/102 351/206 |
| 2016/0317028 | A1 * | 11/2016 | Murata | A61B 3/102 |
| 2016/0345820 | A1 * | 12/2016 | Frisken | A61B 3/0025 |

FOREIGN PATENT DOCUMENTS

| | | |
|---|---|---|
| JP | H06-165784 A | 6/1994 |
| JP | H08-288197 A | 11/1996 |
| JP | 10-210454 | 8/1998 |
| JP | 2001-330558 A | 11/2001 |
| JP | 2006-526790 A | 11/2006 |
| JP | 2010-515919 A | 5/2010 |
| JP | 2011-027715 A | 2/2011 |
| JP | 2012-10776 | 1/2012 |

OTHER PUBLICATIONS

"Evaluation of optical coherence quantitation of analytes in turbid media by use of two wavelengths" to Sathyam et al. (App. Optics, vol. 38 N. 10, p. 2097; 1999).* http://www.thefreedictionary.com/correspond.*

Fercher et al. "Optical coherence tomography—principles and applications" (Rep. Prog. Phys. 66 (2003) 239-303).*

Knuttel et al. "Low-coherence reflectometry for stationary lateral and depth profiling with acousto-optic deflectors and a CCD camera"; Optics Letters / vol. 19, No. 4 / Feb. 15, 1994.*

Schmitt "Optical Coherence Tomography (OCT): A Review"; IEEE Journal of Selected Topics in Quantum Electronics, vol. 5, No. 4, Jul./Aug. 1999.*

Lan et al. "Design of high-performance adaptive objective lens with large optical depth scanning range for ultrabroad near infrared microscopic imaging"; Biomedical Optics Express 3362; Sep. 1, 2015 | vol. 6, No. 9.*

Medical Photonics No. 1. p. 29-33.

Medical Photonics No. 7. p. 58-64.

Office Action, dated Jul. 30, 2015, which issued during the prosecution of Chinese Patent Application No. 201310544611.8, which corresponds to the present application.

Notification of Reasons for Refusal, dated May 31, 2016, which issued in Japanese Patent Application No. 2013-011296, which corresponds to the present application (English translation attached).

* cited by examiner

OPTICAL TOMOGRAPH AND OPTICAL TOMOGRAPHIC METHOD

CROSS-REFERENCE TO RELATED APPLICATION

This application claims the priority of Japanese Patent Application No. 2013-011296 filed Jan. 24, 2013, which is incorporated herein by reference in its entirety.

BACKGROUND

The present invention relates to an optical tomograph and an optical tomographic method, especially relates to optical tomographic technique that visualizes the distribution in an optical tomographic direction of a substance to be examined.

Recently, optical coherence tomography (OCT) that forms images showing a superficial shape and an internal shape of a measured object using light beams from a laser and others attracts attention (refer to Medical Photonics No. 1 (2010), pp. 29-33 and Medical Photonics No. 7 (2011), pp. 58-64). As OCT has no invasiveness into a human body differently from X-ray CT, the development of application in a medical field and a biological field especially is expected. For example, in an ophthalmic field, a device that forms images of an eyeground, a cornea and others is being realized.

In such OCT, spectrum-domain OCT is adopted. In the spectrum-domain OCT, as a reference mirror is not required to be driven in measurement differently from conventional type time-domain OCT, high-speed measurement is possible. In the spectrum-domain OCT, for example, an ophthalmoscope that acquires various information in a direction of the depth of an examined eye by radiating near infrared measurement light of short coherence length, that is, measurement light having a broad-band wavelength spectrum toward the examined eye, diffracting interference light into each wavelength component using a diffraction grating and others after its reflected light is made to interfere with reference light, instructing a light receiving element to receive diffracted luminous fluxes and analyzing their received signals is known (refer to Japanese Unexamined Patent Application Publication No. 1999-325849). The realization of a function that presents effective information in medical diagnosis by extracting the information of specific structure such as a blood vessel from three-dimensional tomographic image data by signal processing utilizing such high-speed OCT and plainly displaying this is expected.

In the meantime, for a method of measuring the distribution of a blood vessel using spectral information, a method (Narrow band imaging (NBI)) of sensing a hemoglobin component included in a blood vessel by diffracted light, roughly distinguishing the depth of the blood vessel and visualizing it and a method (Hemoglobin index: IHb) of measuring the local density distribution of hemoglobin are known. As for NBI, refer to Japanese Patent No. 3559755 and as to IHb, refer to Japanese Unexamined Patent Application Publication No. 1998-210454.

Further, for an example of a diagnosis system that combines results acquired in OCT and a blood analyzer by image processing, Japanese Unexamined Patent Application Publication No. 2012-10776 exists.

SUMMARY

However, for a result of measurement in OCT described in Japanese Unexamined Patent Application Publication No. 1999-325849, acquired information is only structural information and for example, no great difference is made between signals of organs such as a blood vessel and a lymphatic vessel which are different in a function though they have the same tubular structure. Therefore, when a blood vessel is detected by signal processing, a problem that tubular structure such as the structure of a lymphatic vessel except the blood vessel is also simultaneously detected occurs. In the meantime, as resolution in depth is low in the methods such as NBI and IHb utilizing spectral information respectively described in Japanese Patent No. 3559755 and Japanese Unexamined Patent Application Publication No. 1998-210454, the depth information of a blood vessel cannot be acquired at high resolution realized in OCT. According to the method disclosed in Japanese Unexamined Patent Application Publication No. 2012-10776 in which OCT and a spectral blood analyzer are used together, spectral information is mainly acquired from only a surface of an observed sample and it is difficult to analyze blood in a tomographic direction though it is enabled in OCT.

The analysis of blood has been discussed for an example, however, even if a substance except blood included in a blood vessel is examined, it is difficult in view of each measurement principle to simultaneously perform spectral evaluation and measurement according to OCT. In OCT, measurement light of short coherence length, that is, measurement light having a broad-band wavelength spectrum is required to be radiated to acquire an optical tomographic image and in high-speed measurement, the wavelength spectrum is utilized for acquiring structural information in a direction of depth. In the meantime, in spectral evaluation, optical variation proper to an examined object is extracted from an acquired spectrum. That is, it is difficult to simultaneously evaluate both and as a result, configuration in which separate evaluation systems are combined is also adopted in Japanese Unexamined Patent Application Publication No. 2012-10776.

The present invention is made in view of such a situation and provides an optical tomograph and an optical tomographic method that enable optical tomography by a method different from OCT in view of spectral characteristics of a substance to be examined and simultaneously enable displaying the distribution in a tomographic direction of the substance to be examined.

It is desirable that the optical tomograph according to the present invention includes a light source unit, an optical imaging head unit, a photodetection unit, a control unit, a signal processing unit and an information input-output unit.

The light source unit radiates laser light of at least two different wavelengths. The optical imaging head unit includes a first optical element that splits a luminous flux including the laser light of different wavelengths outgoing from the light source unit into first and second luminous fluxes, an objective lens that converges the first luminous flux on a sample, irradiates the sample and receives reflected light reflected from the sample as signal light, a reflector that reflects the second luminous flux as reference light without radiating the second luminous flux onto the sample, a second optical element that multiplexes the signal light and the reference light and an actuator that drives the objective lens at least in a direction of an optical axis. The photodetection unit includes plural photodetectors and an interference optical system that makes the signal light and the reference light interfere on each photodetector in mutually different phase relation. The control unit controls the actuator and a state in which laser light of different wavelengths is emitted. The signal processing unit acquires the distribution on a section of an object of examination in the sample by acquiring a detection signal by executing operation using the outputs of the plural photodetectors for input every wavelength and calculating the ratio of detection signals of different wavelengths every position in the sample. The information input-output unit includes an input device that inputs a position to be observed in the sample to the optical imaging head unit and a display that displays the distribution of on the section of the object of examination.

Hereby, as in the plural photodetectors, the reference light and the signal light which is hit on the sample and is reflected are multiplexed and the signal light can be amplified by interference effect, the minute reflected signal can be detected at high signal-to-noise ratio (S/N). That is, sensitive optical tomography is enabled. Further, as the ratio of detection signals of plural wavelengths reflects the abundance ratio of the substance to be examined, a result of the distribution on the section of the object of examination can be also simultaneously displayed.

For the configuration of a first concrete optical tomograph, a light source unit includes at least two laser elements for radiating different wavelengths and an optical element that multiplexes luminous fluxes from at least the two laser elements, and an objective lens used in an optical imaging head unit has configuration corresponding to at least the two different wavelengths. Substances to be examined are increased by increasing wavelengths which can be handled in the light source unit and precision in measuring an object of examination can be enhanced.

For the configuration of a second concrete optical tomograph, an optical system can be miniaturized by using a 2-wavelength semiconductor laser that can selectively radiate two wavelengths in a light source unit, using four photodetectors in a photodetection unit and using a diffraction grating in an interference optical system to lead a luminous flux onto the plural photodetectors. At this time, as interference light of different wavelengths can be received by the same photodetector by making A meet an expression (1) when the wavelengths of the 2-wavelength semiconductor laser are $\lambda_1$, $\lambda_2$ ($\lambda_1 > \lambda_2$), the quantity of a shift of an emission point on an outgoing plane of the 2-wavelength semiconductor laser is $\Delta S$, pitch of the diffraction grating is d, distance from the diffraction grating to detection planes of the four photodetectors is L, imaging magnification on an emission point plane of the 2-wavelength semiconductor laser and on the detection plane of the photodetector is M and the size of the largest photodetector of the four photodetectors is A, the photodetector can be miniaturized.

[Mathematical expression 1]

$$L \times \left\{ \tan\left(\arcsin\left(\frac{\lambda_1}{d}\right)\right) - \tan\left(\arcsin\left(\frac{\lambda_2}{d}\right)\right) \right\} + M\Delta S \leq \quad (1)$$

$$A_{min} \leq L \times \tan\left(\arcsin\left(\frac{\lambda_1}{d}\right)\right)$$

Further, in the signal processing unit, an effect of an emission point shift caused by the use of the 2-wavelength semiconductor laser can be nullified by storing the quantity of a shift of a focal point on a sample accompanied by the quantity of the shift of the emission point of the 2-wavelength semiconductor laser in a memory module, operating the ratio of detection signals of two wavelengths based upon positional data acquired by correcting the quantity of the shift of the focal point extracted from the memory module and displaying a result of the distribution on a section of an object of examination. As many optical parts can be used in common in the measurement of different wavelengths because the 2-wavelength semiconductor laser, the diffraction grating, the photodetector in suitable size shown in the above expression (1) and the signal processing unit that corrects the quantity of the shift of the focal point are provided, the miniaturization and the reduction of a cost of the optical tomograph are enabled.

For the configuration of a third concrete optical tomograph, a light source unit, an optical imaging head unit, a photodetection unit, a control unit and a signal processing unit are provided with a connector, and the light source unit, the optical imaging head unit and the photodetection unit are electrically connected to the control unit and the signal processing unit via a connecting unit and the connector respectively including wiring. Because of such configuration, an analyzer configured by the control unit and the signal processing unit can be kept at a distance by only extending wiring length from the light source unit, the optical imaging head unit and the photodetection unit respectively integrated in a module and optical tomography in a state in which the analyzer recedes in a backyard is enabled.

For the configuration of a fourth concrete optical tomograph, a light source unit, an optical imaging head unit and a photodetection unit are provided with a wiring connector and an optical fiber connector, and a control unit and a signal processing unit are provided with a wiring connector. Besides, the light source unit, the optical imaging head unit and the photodetection unit are electrically connected to the control unit and the signal processing unit via a connecting unit and the wiring connector respectively including wiring. Further, the optical imaging head unit is optically connected to the light source unit and the photodetection unit via the connecting unit and the optical fiber connector respectively including an optical fiber. Not only the replacement and the maintenance of the optical imaging head unit are simplified by such configuration but only the optical imaging head unit can be moved at a distance by extending wiring length, and optical tomography can be made facile observation using a microscope.

In an optical tomographic method according to the present invention, a luminous flux including laser light of plural wavelengths different in optical sensitivity for material to be examined is split into first and second luminous fluxes, the first luminous flux is radiated with the first luminous flux focused on a sample, signal light reflected from the sample is led to plural photodetectors, the second luminous flux is led to the plural photodetectors as reference light without radiating the second luminous flux toward the sample, and the signal light and the reference light are made to optically interfere on the plural photodetectors in a state in which optical phase relation between both is mutually different. The distribution of an object of examination in a tomographic image of the sample is visualized for the tomography of the sample by operating using outputs of the plural photodetectors for input every wavelength, acquiring a result of the operation as a detection signal that reflects internal structure of the sample at a focal point of the first luminous flux, operating the ratio in intensity of the detection signals at each wavelength at the same focal point in the sample and acquiring the detection signal, varying a focused position of the first luminous flux in the sample.

Optical tomography using a high coherent light source such as a general semiconductor laser, that is, a single-wavelength light source is enabled by using homodyne optical interference technique different from OCT as described above. Further, the distribution in an optical axis direction of a substance to be examined can be visualized by preparing a light source unit in which plural wavelengths different in the optical sensitivity of the substance to be examined are available and comparing results of measurement at the plural wavelengths.

Besides, the photodetector for acquiring detection signals at plural wavelengths can be shared by radiating luminous fluxes having plural wavelengths onto a sample in time division. This is useful for the miniaturization of the optical tomograph and the simplification of signal transmission.

Further, a detection signal independent of an interferential state can be acquired by regulating operation even if an optical system is in an incomplete or unstable situation. Concretely, four photodetectors for acquiring an interference signal are installed so that phases of reference light and signal light are mutually different by substantially 180 degrees on the first photodetector and on the second photodetector, the phases are mutually different by substantially 180 degrees on the third photodetector and on the fourth photodetector, and the phases are different by substantially 90 degrees on the first photodetector and on the third photodetector as to relation in a phase between the reference light and the signal light. Hereby, four phases shifted by substantially 90 degrees in phase relation of substantially 360 degrees can be simultaneously detected. As a detection signal varies in a sinewave according to the variation of an optical phase of 360 degrees, a signal at an arbitrary phase can be regenerated by operation by observing four signals out of phase by substantially 90 degrees. That is, stable detection at an arbitrary phase is realized. For the operation, the square of a differential signal between the first photodetector and the second photodetector and the square of a differential signal between the third photodetector and the fourth photodetector are summed.

At this time, even if an optical system and others for acquiring four interference signals are shifted from an ideal state, a fixed output signal independent of an interference phase can be acquired by operation called phase diversity detection. Besides, three photodetectors for acquiring an interference signal are installed so that phases of reference light and signal light are mutually different by 120 degrees from the first photodetector to the third photodetector, signals output from the first to the third photodetectors are operated in a quadratic polynomial, and the signals may be also output as a detection signal. The miniaturization of the photodetection unit and the simplification of an electric circuit can be realized by reducing the number of the photodetectors.

According to the present invention, the optical tomograph that simultaneously executes interference type optical tomography by the method different from OCT and the display of the distribution in an optical axis direction of a substance to be examined can be provided.

A problem, configuration and effect except the above-mentioned will be clarified by the description of the following embodiments.

DETAILED DESCRIPTION

Figure 1:
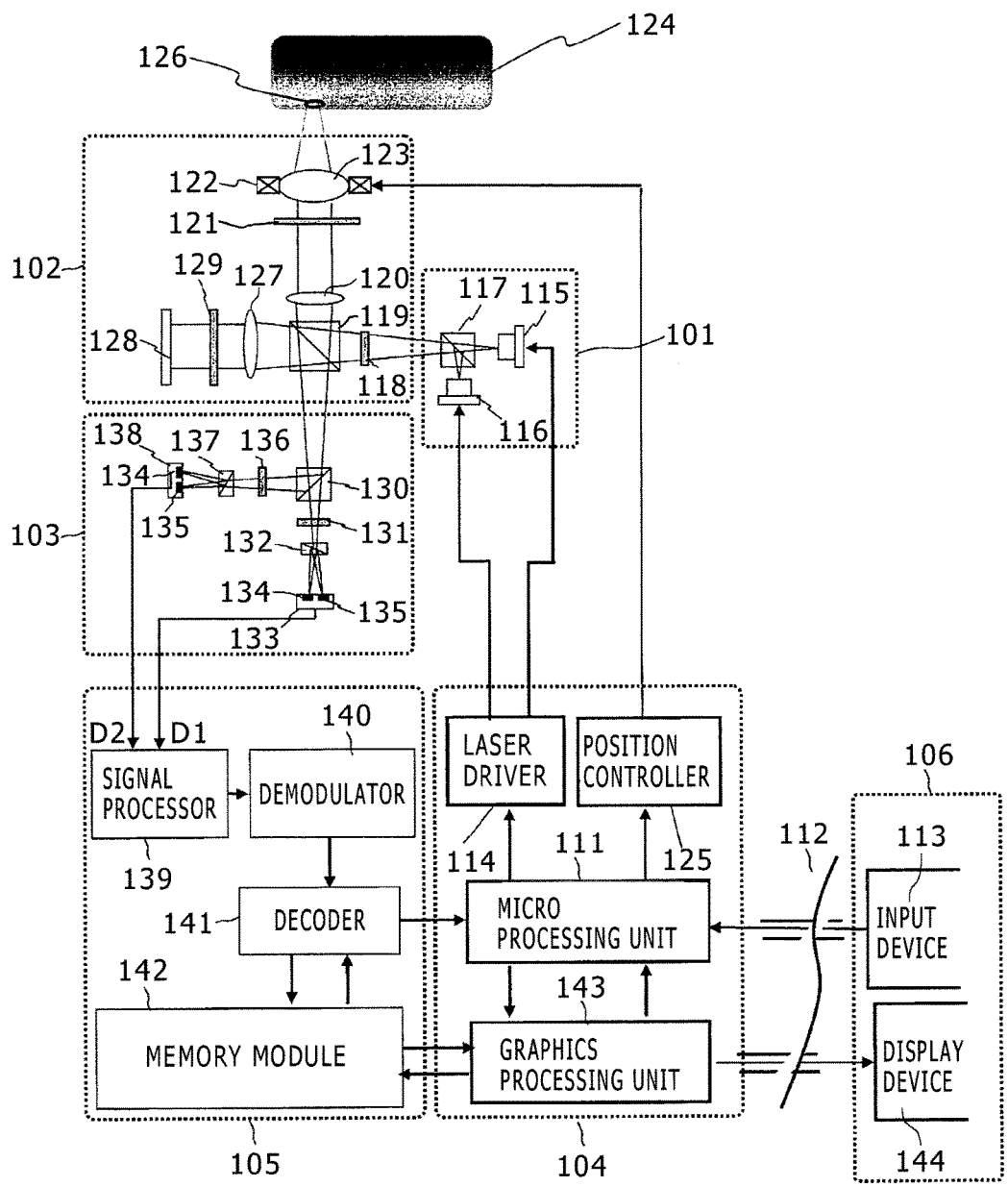
FIG. 1 is a block diagram showing an optical tomograph equivalent to a first embodiment of the present invention.

Referring to the drawings, embodiments of the present invention will be described below.

First Embodiment

FIG. 1 is a block diagram showing an optical tomograph equivalent to a first embodiment of the present invention. The optical tomograph includes a light source unit 101, an optical imaging head unit 102, a photodetection unit 103, a control unit 104, a signal processing unit 105 and an information input-output unit 106.

First, the operation of this tomograph for observing optical hierarchical structure will be described.

A micro processing unit 111 included in the control unit 104 generates a modulating signal for measurement corresponding to an optical tomographic condition transmitted from an input device 113 included in the information input-output unit 106 connected to a control signal cable 112 and transmits the modulating signal to a laser driver 114.

The light source unit 101 includes a first light source 115, a second light source 116 and a dichroic mirror 117. The first light source 115 and the second light source 116 are alternately driven in time division by modulating signals respectively output from the laser driver 114. In this embodiment, a semiconductor laser having a wavelength of 780 nm is used for the first light source and a semiconductor laser having a wavelength of 660 nm is used for the second light source. Besides, the dichroic mirror 117 is modulated so that each luminous flux after passing the dichroic mirror 117 of both light sources has the same optical axis by designing so that the dichroic mirror transmits the wavelength of the first light source 115 and reflects the wavelength of the second light source 116. Hereby, the simplification of an optical system using plural wavelengths is realized.

A luminous flux which is outgoing from the first light source 115 or the second light source 116 and which passes the dichroic mirror 117 is led into the optical imaging head unit 102. Next, the luminous flux led into the optical imaging head unit 102 is transmitted in a λ/2 (half-wave) plate 118. An optical axis of the λ/2 plate 118 is set to 22.5 degrees with a horizontal direction and the luminous flux is polarized by 45 degrees. A polarized beam splitter 119 includes a property that reflects vertically polarized light and transmits horizontally polarized light (any polarized beam splitter used in the present invention includes the same property) and the polarized light is split into a vertically polarized luminous flux reflected by the polarized beam splitter 119 and a horizontally polarized luminous flux transmitted by the polarized beam splitter 119. Out of these, the reflected luminous flux passes a λ/4 (quarter-wave) plate (its axial direction: 45° with a horizontal polarization direction) 121 after the reflected luminous flux is made parallel light by a first collimating lens 120 and is converged into an inside of a sample 124 by a compatible objective lens for two wavelengths 123 mounted in an actuator 122. In this case, reflected light corresponding to depth of optical axis is acquired from the sample 124 by driving the actuator 122 mounting the compatible objective lens for two wavelengths 123 using a control signal from a position controller 125 and scanning a light spot 126 in a direction of an optical axis.

The actuator can be configured by a magnetic circuit having a yoke and a permanent magnet, a moving part to which the objective lens and driving coils are attached, a fixed part that holds the moving part and a supporting member that elastically supports the moving part connected to the fixed part for example. When current is made to flow into the first driving coil in a magnetic field generated by the magnetic circuit having the yoke and the permanent magnet, Lorentz's force is generated and the moving part is driven in the direction of the optical axis. Similarly, when current is made to flow into the second driving coil in the magnetic field generated by the magnetic circuit having the yoke and the permanent magnet, Lorentz's force is generated and the moving part is driven in a direction perpendicular to the optical axis. That is, the actuator is suitable for enabling scanning in the direction of the optical axis and in the direction perpendicular to the optical axis with the objective lens by varying current applied to the driving coil, scanning the light spot and acquiring an optical tomographic image. Besides, the compatible objective lens for two wavelengths 123 is a lens having well-known configuration that can converge luminous fluxes of different two wavelengths in the same light spot and in this embodiment, a lens that can converge the luminous flux having the wavelength of 780 nm and the luminous flux having the wavelength of 660 nm in the same position is used.

The reflected light (hereinafter called signal light) from the sample 124 follows an optical path reverse to that in radiation and is incident upon the polarized beam splitter 119 in a state of horizontal polarization. In the meantime, a luminous flux (hereafter called reference light) transmitted in the polarized beam splitter 119 is reflected in an opposite direction by a mirror 128 after the luminous flux is made a parallel flux by a collimating lens 127, its direction of polarization is made vertical polarization because the luminous flux is made to pass a λ/4 (quarter-wave) plate 129 (its axial direction: 45° with the direction of horizontal polarization) twice, and the luminous flux is incident upon the polarized beam splitter 119 again. In the beam splitter, the signal light and the reference light are multiplexed in a state in which polarization is perpendicular and are led into the photodetection unit 103.

The multiplexed luminous flux led into the photodetection unit 103 is divided into transmitted light and reflected light in two by an unpolarized half beam splitter 130. The transmitted light passes a λ/2 (half-wave) plate 131 an optical axis of which is set to 22.5° with a horizontal direction, is polarized by 45 degrees, and is separated into a p-polarized component and an s-polarized component by Wollaston prism 132. The separated luminous fluxes are incident upon photodiodes 134, 135 of a differential detector 133 and an electric signal proportional to the difference in intensity is output from the differential detector 133. Similarly, a luminous flux reflected by the unpolarized half beam splitter 130 is separated by a Wollaston prism 137 after the luminous flux passes a λ/4 (quarter-wave) plate 136 an optical axis of which is set to 45° with the horizontal direction and the separated luminous fluxes are detected by a differential detector 138. As described later, the luminous fluxes after they are separated by the Wollaston prisms 132, 137 are all interferential light in which the signal light and the reference light interfere and the outputs of the differential detectors 133, 138 are acquired by respectively extracting an interference component.

The outputs of the differential detectors 133, 138 are transmitted to the signal processing unit 105. The output signals are transmitted to a digital signal processor 139 provided to the signal processing unit 105 and there, a detection signal as the optical intensity of reflected light that reflects optical hierarchical structure can be acquired. The acquired detection signal is transmitted to a decoder 141 after the detection signal is demodulated in a demodulator 140 and is stored in a memory module 142. When the detection signal stored in the memory module 142 is transmitted to a display device 144 provided to the information input-output unit 106 by a graphics processing unit 143 provided to the control unit 104, an operator can verify an optical tomographic image in a designated position.

Next, a principle in which interferential light is generated by the above-mentioned operation, hereby, which is different from OCT and in which reflected light caused by optical hierarchical structure is acquired will be described. As the luminous flux incident upon the unpolarized half beam splitter 130 includes the signal light as the p-polarized component and includes the reference light as the s-polarized component, its polarized state represented by Jones vector is as shown in the following expression.

[Mathematical expression 2]

$$\begin{pmatrix} E_r \\ E_s \end{pmatrix} \quad (2)$$

In this case, "$E_s$" denotes an electric field of the signal light and "$E_r$" denotes an electric field of the reference light. Besides, a first component of this vector denotes p-polarized light and a second component denotes s-polarized light. Jones vector after this luminous flux is transmitted in the unpolarized half beam splitter 130 and passes the λ/2 plate 131 is as follows.

[Mathematical expression 3]

$$\begin{pmatrix} \cos 45° & -\sin 45° \\ \sin 45° & \cos 45° \end{pmatrix} \begin{pmatrix} E_r/\sqrt{2} \\ E_s/\sqrt{2} \end{pmatrix} = \begin{pmatrix} (E_r - E_s)/2 \\ (E_r + E_s)/2 \end{pmatrix} \quad (3)$$

Next, as the luminous flux is separated into a p-polarized component and an s-polarized component by the Wollaston prism 132, electric fields of the separated luminous flux are as follows, and the signal light and the reference light are superimposed to be, that is, interferential light.
[Mathematical Expression 4]

$$\tfrac{1}{2}(E_r - E_s) \quad (4)$$

$$\tfrac{1}{2}(E_r + E_s) \quad (5)$$

In the meantime, Jones vector after light reflected by the unpolarized half beam splitter 130 passes the λ/4 plate 136 is as follows.

[Mathematical expression 5]

$$\frac{1}{\sqrt{2}}\begin{pmatrix} i - \cos 90° & \sin 90° \\ \sin 90° & i + \cos 90° \end{pmatrix}\begin{pmatrix} E_r/\sqrt{2} \\ -E_s/\sqrt{2} \end{pmatrix} = \begin{pmatrix} i(E_r + iE_s)/2 \\ (E_r - iE_s)/2 \end{pmatrix} \quad (6)$$

Next, as the luminous flux is separated into a p-polarized component and an s-polarized component by the Wollaston prism 137, electric fields of the separated luminous flux are as follows.
[Mathematical Expression 6]

$$\tfrac{1}{2}(E_r + iE_s) \quad (7)$$

$$\tfrac{1}{2}(E_r - iE_s) \quad (8)$$

The signal light and the reference light are also superimposed to be, that is, interferential light. Accordingly, the intensity of four interferential lights is respectively as follows.
[Mathematical Expression 7]

$$|\tfrac{1}{2}(E_r - E_s)|^2 = \tfrac{1}{4}|E_r|^2 + \tfrac{1}{4}|E_s|^2 - \tfrac{1}{2}|E_r E_s|\cos\Delta\phi \quad (9)$$

$$|\tfrac{1}{2}(E_r + E_s)|^2 = \tfrac{1}{4}|E_r|^2 + \tfrac{1}{4}|E_s|^2 + \tfrac{1}{2}|E_r E_s|\cos\Delta\phi \quad (10)$$

$$|\tfrac{1}{2}(E_r + iE_s)|^2 = \tfrac{1}{4}|E_r|^2 + \tfrac{1}{4}|E_s|^2 + \tfrac{1}{2}|E_r E_s|\sin\Delta\phi \quad (11)$$

$$|\tfrac{1}{2}(E_r - iE_s)|^2 = \tfrac{1}{4}|E_r|^2 + \tfrac{1}{4}|E_s|^2 - \tfrac{1}{2}|E_r E_s|\sin\Delta\phi \quad (12)$$

A first term denotes an intensity component of the signal light, a second term denotes an intensity component of the reference light, and a third term denotes the interference of the signal light and the reference light. Δφ denotes a phase of the signal light based upon a phase of the reference light and this is the modulating signal to be detected. The outputs of the differential detectors 133, 138 are expressed as shown by the following expressions because the outputs are proportional to difference in intensity between these demultiplexed lights and are outputs proportional to the above-mentioned terms showing interference. To simplify the description, the conversion efficiency of the photodetection unit is set to 1.
[Mathematical Expression 8]

$$D_1 = |E_r E_s|\cos\Delta\phi \quad (13)$$

$$D_2 = |E_r E_s|\sin\Delta\phi \quad (14)$$

After the above-mentioned outputs of the differential detectors 133, 138 are first converted from analog to digital in the digital signal processor 139, they are input to an arithmetic circuit and a result of the following operation is output.
[Mathematical Expression 9]

$$\sqrt{D_1^2 + D_2^2} = |E_r E_s| \quad (15)$$

As described above, a signal proportional to a square root of an intensity value of the signal light can be also acquired by generating the interferential light of the signal light and the reference light and detecting it. If a square root in the expression (15) is omitted, it is a signal proportional to the intensity value of the signal light. As the expression (15) includes no phase term of an electric field, the advanced correction required in the existing optical amplification technique and having the precision of a nanometer of optical path length is not required. That is, simple optical interference amplification technique is realized by using this detection method.

Next, the reason why optical tomography is possible will be described using this detection technique. In this detection method, an object plane of the light spot 126 on which the compatible objective lens for two wavelengths 123 is focused and observation planes of the four photodiodes 134, 135 are related to image formation. At this time, in a position distant from the object plane in an optical tomographic direction, a light spot 126 is defocused to be in a state in which the phase distribution of light is out of order. This shows a state in which the phase relation of the signal light and the reference light is out of order on the photodiodes 134, 135 to be the observation planes and at this time, sufficient signal amplification cannot be realized.

In the meantime, as the signal light and the reference light in a focused state are in phase in the photodetection unit, signal amplification shown in the expression (15) is realized. These results show that only when a boundary made of different materials exists on the object plane, that is, only when reflectance varies, signal amplification is performed and in the meantime, show that in general optical tomography, a stray light component caused in the defocused state can be cut.

Figure 2:
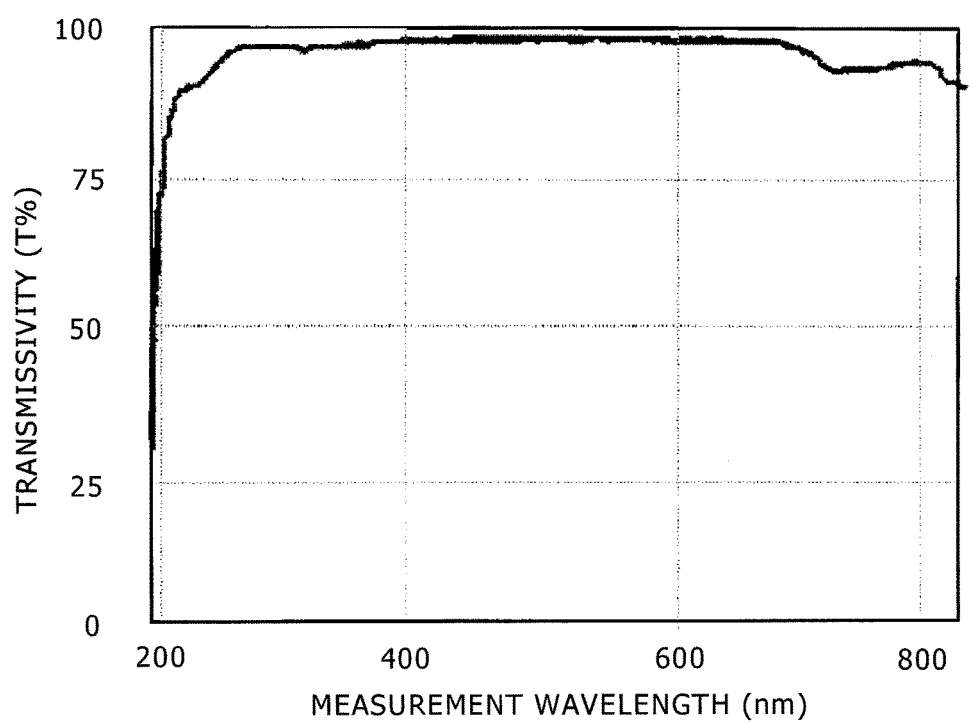
FIG. 2 shows spectral characteristics (transmissivity) of a substance to be examined.

In this embodiment, water having spectral characteristics shown in FIG. 2 in the thickness of 20 mm is used for a substance to be examined. As known from FIG. 2, the water has the transmissivity of 95% for light having the first wavelength of 780 nm and has the transmissivity of 100% for light having the second wavelength of 660 nm. Besides, a film having the thickness of 10 μm and including the same substance by 2 wt. % is prepared as a sample for optical tomography. For the material of the film, optical plastic material that does not absorb both the first and second wavelengths is used.

Figure 3:
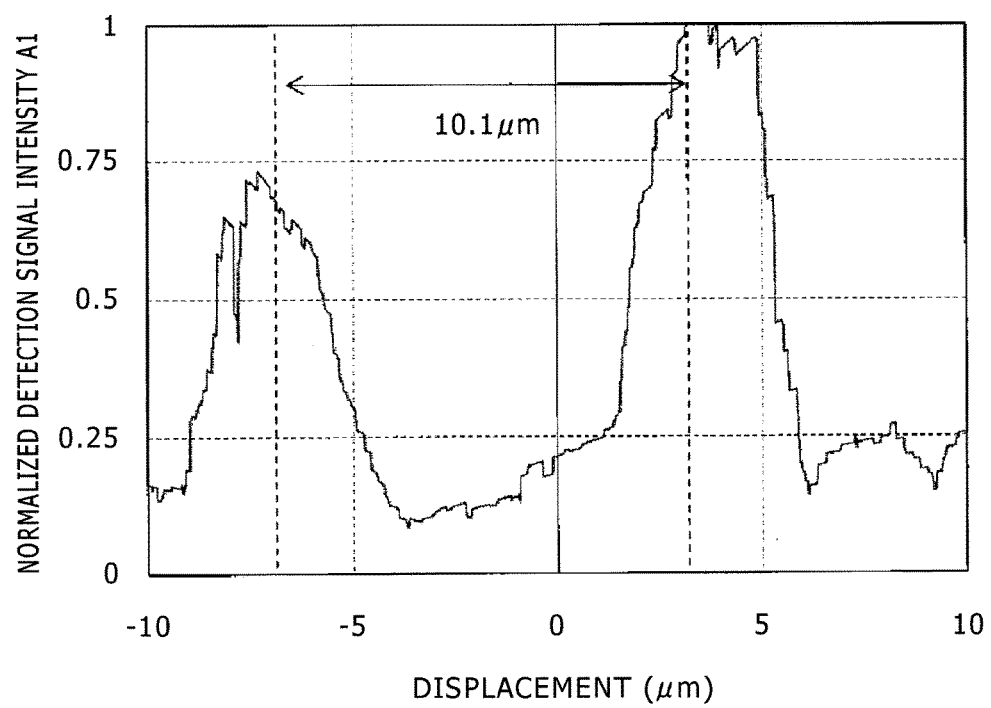
FIG. 3 shows the distribution in an optical tomographic direction of normalized detection signal intensity acquired at a first wavelength.

FIG. 3 shows the distribution in the optical tomographic direction of normalized detection signal intensity acquired at the first wavelength. As known from FIG. 3, when the compatible objective lens for two wavelengths 123 is displaced in the optical tomographic direction in this photodetection method, two detection peaks can be verified. Distance between these detection peaks is 10.1 μm and the thickness itself of the sample for optical tomography is shown. Besides, in FIG. 3, the width of the detection peak reflects measurement precision in optical tomography and in this embodiment, measurement precision at the first wavelength of 780 nm is 3 μm in full width at half maximum. The width of the detection peak in a principle of this photodetection technique is in conformity with the depth of a focus of the light spot 126.

Figure 4:
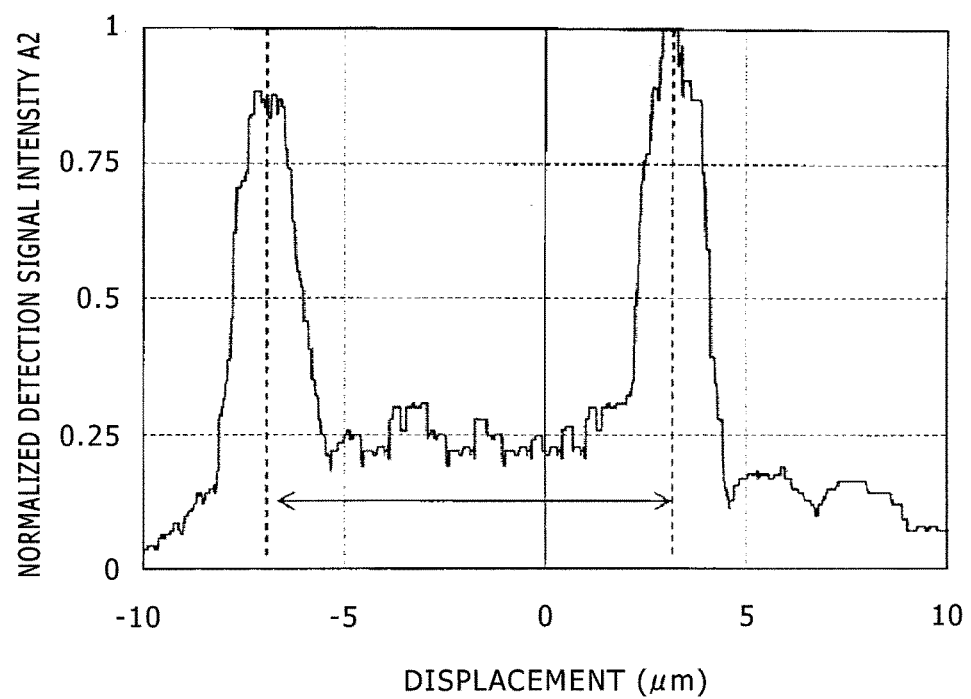
FIG. 4 shows the distribution in the optical tomographic direction of normalized detection signal intensity acquired at a second wavelength.

FIG. 4 shows the distribution in the optical tomographic direction of normalized detection signal intensity acquired at the second wavelength. As known from FIG. 4, when the compatible objective lens for two wavelengths 123 is displaced in the optical tomographic direction as in FIG. 3, two detection peaks can be verified. Besides, distance between the detection peaks is 10.0 μm and is also substantially equal. In the meantime, FIG. 4 is different from FIG. 3 at the following two points. For the first point of difference, the detected width of the peak in FIG. 4 is narrower than that in FIG. 3. This shows that measurement precision is enhanced. The reason is that the depth of the focus of the light spot 126 becomes narrower by using a high-power lens having a short wavelength and a high numerical aperture. For the second point of difference, the variation of luminous energy inside the film in FIG. 4 decreases, compared with that in FIG. 3. In measurement using the first wavelength in FIG. 3, as displacement decreases, the height of the detection peak and signal intensity at its intermediate point also decrease. This shows that in the measurement at the first wavelength shown in FIG. 3, the absorption of light occurs when the light is propagated inside the film. In the meantime, in measurement at the second wavelength in FIG. 4, as no absorption of light occurs, no decrease of signal intensity inside the film is verified. This trend is in conformity with the spectral characteristics shown in FIG. 2 of the detection object substance. From results of the measurement shown in FIGS. 3 and 4, the percentage content of the examination object included in the film can be estimated by calculating the ratio of first and second signal intensity.

Figure 5:
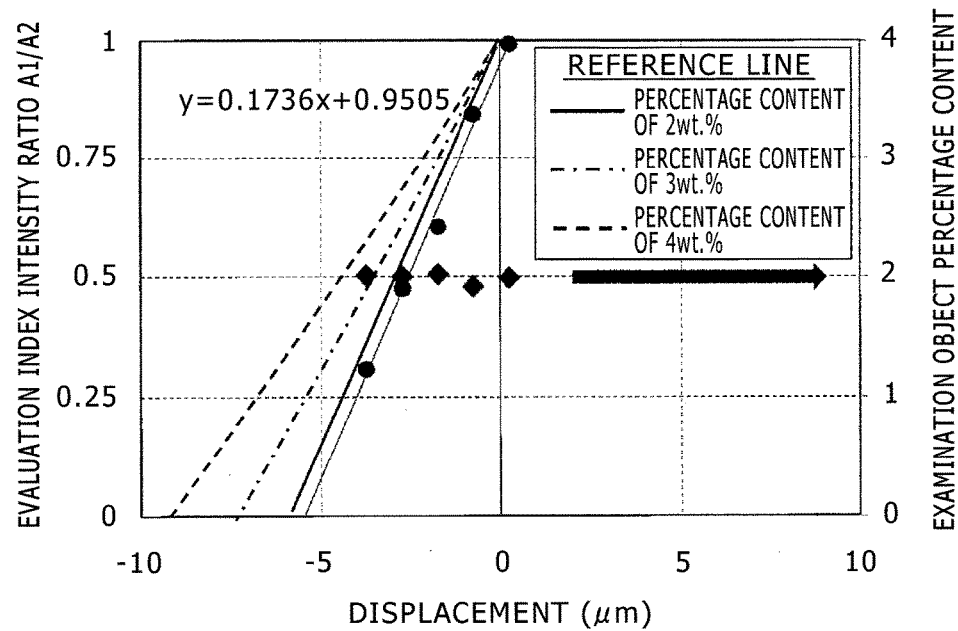
FIG. 5 shows a result of calculating the ratio of detection signal intensity at the first and second wavelengths and the distribution of the percentage content of an examination object.

FIG. 5 shows a result of calculating the ratio of detection signal intensity at the first and second wavelengths and the distribution of the percentage content of an examination object. When the ratio of detection signal intensity is calculated in a range of 0 to −4 μm as displacement except a detection peak caused by structure in optical tomography, the ratio of intensity is substantially in conformity with a line acquired by a reference sample having the percentage content of 2% in the calibration of the tomograph. This shows that in this film, an examination object substance of 2 wt. % uniformly exists in the optical tomographic direction. For a result of the measurement of the reference sample, the measurement of the reference sample can be made unnecessary in the following measurement by measuring the reference sample after the assembly of the tomograph and storing measurement data in the memory module 142.

Second Embodiment

Figure 6:
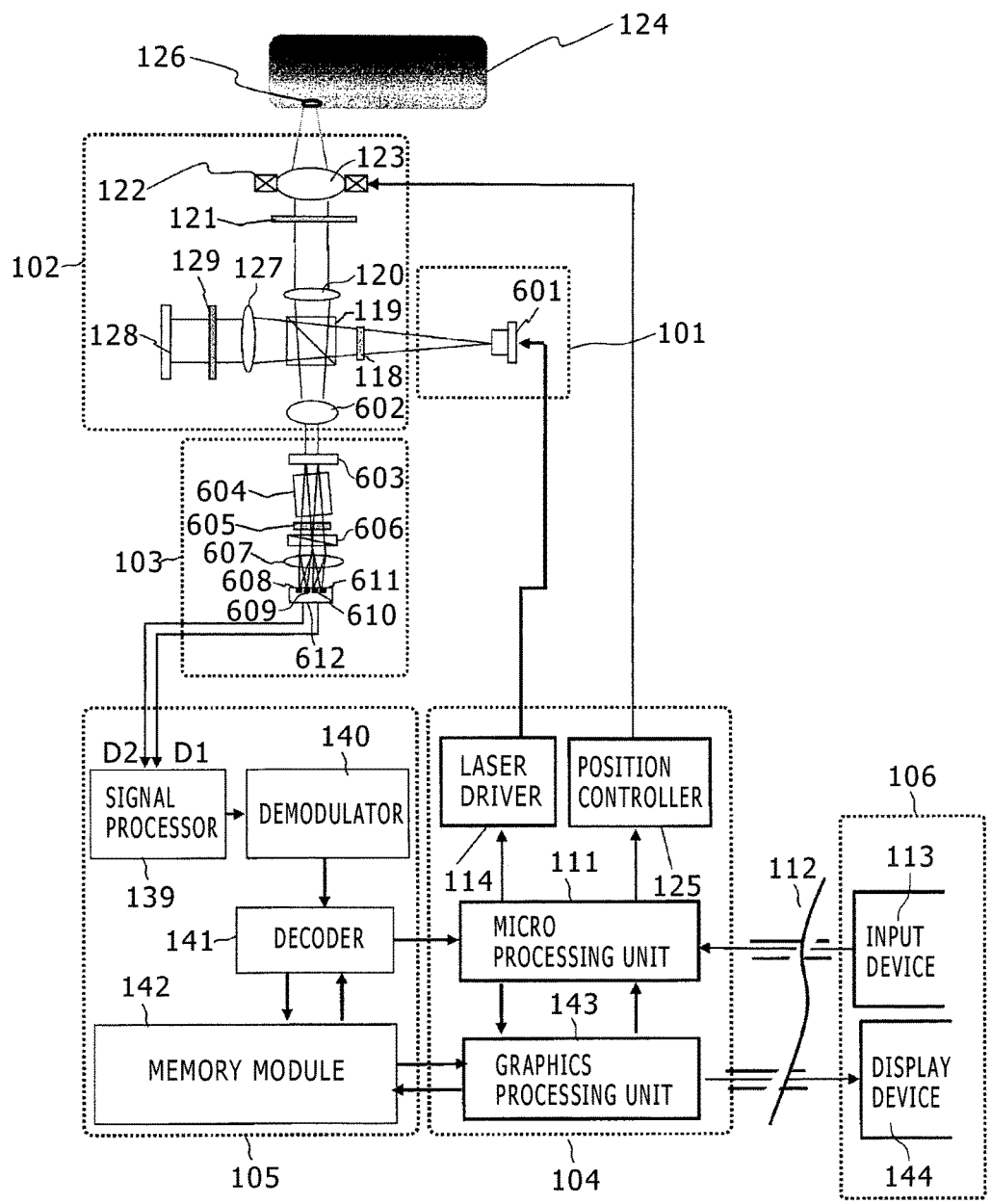
FIG. 6 is a block diagram showing an optical tomograph equivalent to a second embodiment of the present invention.

FIG. 6 is a block diagram showing an optical tomograph equivalent to a second embodiment of the present invention. In this embodiment, the optical tomograph is miniaturized and simplified by using a 2-wavelength semiconductor laser 601 for the light source unit 101 and using an integrated photodetection module for the photodetection unit 103. The basic configuration and the operation of the tomograph are the same as those in the first embodiment. The second embodiment is different in the configuration in that when light is led from an optical tomographic head unit 102 to the photodetection unit 103, a collimating lens 602 is added and collimated light (parallel light) is incident on the integrated photodetection module. Besides, the integrated photodetection module includes a diffraction grating 603, a phase plate 604, a λ/2 (half-wave) plate 605, Wollaston prism 606, a condenser 607, four photodiodes 608 to 611 and a differential detector 612.

First, a function and the configuration of the integrated photodetection module will be described.

Figure 7:
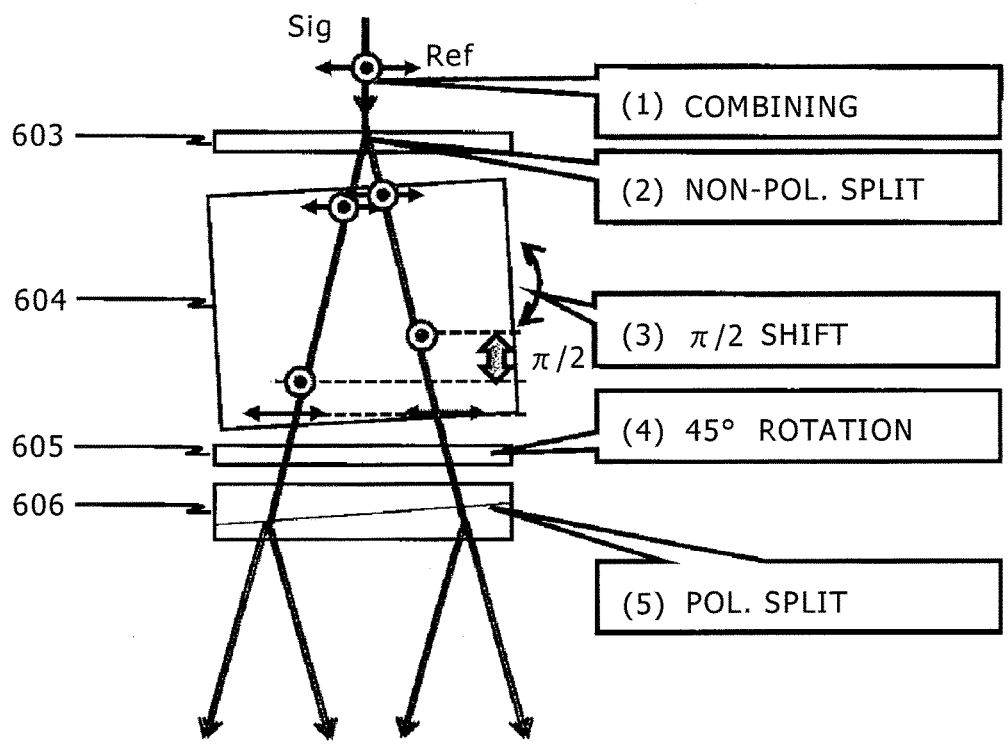
FIG. 7 is a schematic drawing for explaining a function of each optical element of an integrated photodetection module.

FIG. 7 is a schematic drawing explaining a function of each optical element of the integrated photodetection module. In the integrated photodetection module, a luminous flux (1) in which signal light and reference light are multiplexed is first demultiplexed into ± primary diffracted light, that is, two luminous fluxes (2) in the diffraction grating 603, and the two luminous fluxes pass the phase plate 604 arranged with the phase plate inclined so that phase difference of π/2 is made between the two luminous fluxes (3). Afterward, the two luminous fluxes are polarized by the λ/2 plate 605 inclined by 45 degrees (4) and the two luminous fluxes are split into further two for each, that is, total four types of polarized lights each polarization direction of which is different by 90 degrees by Wollaston prism 606 (5).

Figure 8:
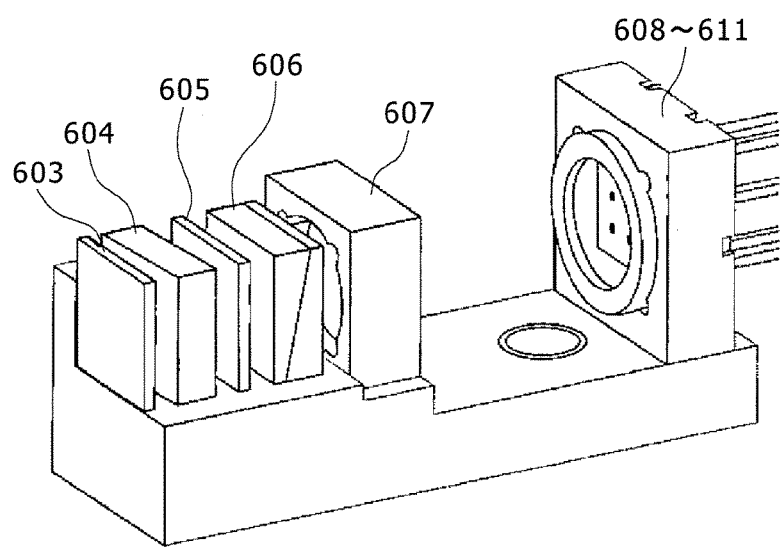
FIG. 8 shows the configuration of the integrated photodetection module.

FIG. 8 shows the integrated photodetection module. The four luminous fluxes which pass the Wollaston prism 606 and each polarization direction of which is different by 90 degrees are converged into the different four photodiodes 608 to 611 by the condenser 607. As a signal output from the differential detector 612 afterward is similar to that in the first embodiment, the details are omitted.

Figure 9:
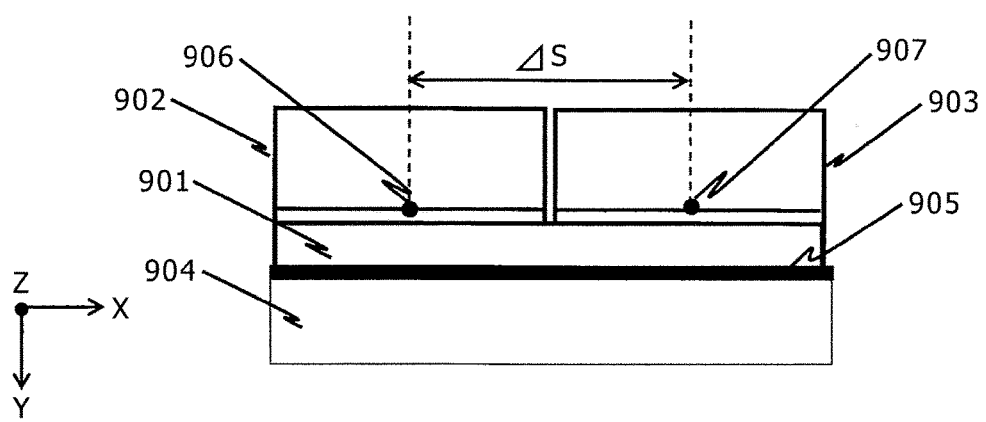
FIG. 9 shows the configuration of a 2-wavelength semiconductor laser.

As shown in FIG. 9, as for the 2-wavelength semiconductor laser, a semiconductor chip (a first light source) 902 and a semiconductor chip (a second light source) 903 are formed on a semiconductor laser substrate 901 in a crystal growth process and both semiconductor laser chips are substantially a rectangular parallelopiped. The semiconductor laser substrate 901 is bonded to a submount 904 via a metalized layer 905.

The submount 904 is a conductor formed by a product ($Al_2O_3.TiC$) manufactured by Altec Lansing Technologies, Inc. and others. Besides, the metallized layer 905 is provided to physically fix the semiconductor laser on the submount and to form an electric contact with the bottom of the semiconductor laser and solder material such as AuSn can be used. A semiconductor laser having multiple quantum well structure can be used for the 2-wavelength semiconductor laser. In these semiconductor lasers, a reflecting film made of $SiO_2$ and $Al_2O_3$ for exciting oscillation by total reflection is formed before and after a cleavage plane of multilayer structure. The 2-wavelength semiconductor laser may also have another configuration using another semiconductor material such as GaAlAs.

In this embodiment, for the semiconductor laser substrate 901, a GaAs substrate is selected, for the material of the semiconductor chip (the first light source) 902, GaAlAs is selected, and for the material of the semiconductor chip (the second light source) 903, InGaAlP is selected. At this time, a wavelength of the first light source is 780 nm, a wavelength of the second light source is 660 nm, and the similar wavelengths to those in the first embodiment are selected. Besides, the first light source 902 and the second light source 903 can be alternately emitted by time sharing by a laser driver 114. The 2-wavelength semiconductor laser has various advantages such as a low cost, miniaturization and power saving driving because the light sources having two types of oscillation wavelengths can be mass-produced on the same substrate, while the semiconductor laser has the following problems.

As in the 2-wavelength semiconductor laser, an emission point 906 in the first light source located in the semiconductor chip 902 and an emission point 907 in the second light source located in the semiconductor chip 903 exist in separate locations, an emission point shift ΔS necessarily exists. The emission point shift ΔS becomes the similar emission point shift both on the object plane to be a light spot focal plane in the sample converged by the objective lens described in the first embodiment and on an observation plane to be a detection plane of the photodiode.

Figure 10:
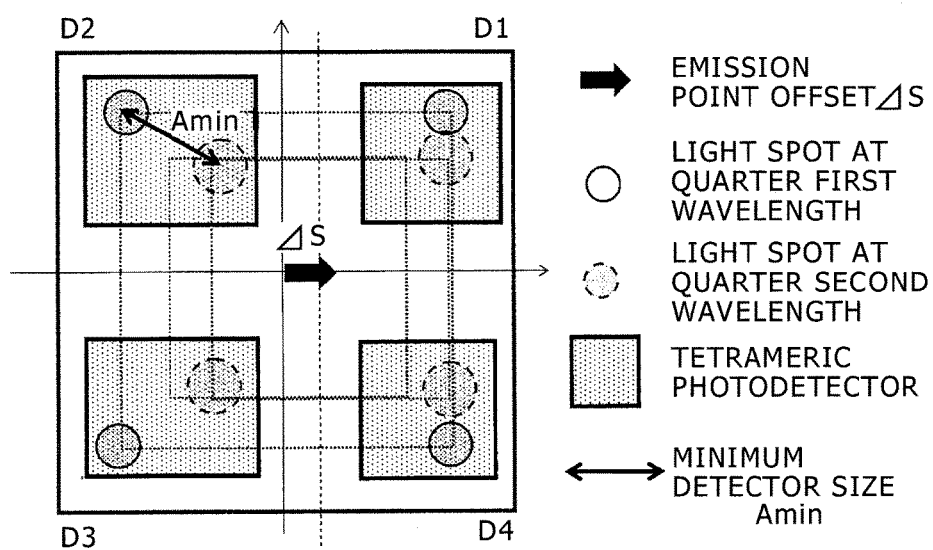
FIG. 10 explains the arrangement of a tetrameric photodetector in an integrated homodyne detection module.

Then, in this embodiment, even if the 2-wavelength semiconductor laser in which the emission point shift exists is used, optical tomography is enabled with simple configuration by devising the size and the arrangement of the photodiodes. FIG. 10 shows the details. The four photodiodes D1 to D4 are required to be arranged on an observation plane of an integrated homodyne detection module. As shown in FIG. 7, on the observation plane, light is divided into four luminous fluxes every wavelength by the diffraction grating 603 and Wollaston prism 606. At this time, when an angle of diffraction from the diffraction grating is α, an incidence angle on the diffraction grating is β, pitch between diffraction gratings is d and a wavelength of incident light is λ, the following relational expression is met.

[Mathematical Expression 10]

$$d \sin \alpha + d \sin \beta = n\lambda \quad (16)$$

"n" denotes the order of diffraction. In this embodiment, as β is 0 degree because incident light is collimated light, the angle α of diffraction from the diffraction grating can be expressed as follows.

[Mathematical expression 11]

$$\alpha = \arcsin\left(\frac{n\lambda}{d}\right) \quad (17)$$

In this case, attention is paid to only ± primary diffracted light (n=1) and when distance between the diffraction grating and a detection plane of a photodetector is L, the quantity of a shift of an emission point on an outgoing plane of the 2-wavelength semiconductor laser is ΔS and imaging magnification of an emission point plane of the 2-wavelength semiconductor laser and a plane of the photodetector is M, distance between each light spot of different wavelengths of the 2-wavelength semiconductor laser on the observation plane can be acquired. This distance between each light spot is a minimum value in size A demanded for the photodetector and can be expressed in the following expression.

[Mathematical expression 12]

$$A_{min} \geq L \times \left\{ \tan\left(\arcsin\left(\frac{\lambda_1}{d}\right)\right) - \tan\left(\arcsin\left(\frac{\lambda_2}{d}\right)\right) \right\} + M\Delta S \quad (18)$$

The imaging magnification M can be acquired by calculating the ratio in a numerical aperture of the collimating lens of the 2-wavelength semiconductor laser and an objective lens before the photodetector. Further, a maximum value in the size A demanded for the photodetector is equal to distance between light spots of ± primary light separated by the diffraction grating and is expressed in the following expression.

[Mathematical expression 13]

$$A_{min} \leq L \times \tan\left(\arcsin\left(\frac{\lambda_1}{d}\right)\right) \quad (19)$$

The same photodetector can also detect the light spots of different wavelengths by coordinating these expressions (18), (19) and using a photodetector that meets the following expression even if the 2-wavelength semiconductor laser in which the emission point shift exists is used.

[Mathematical expression 14]

$$L \times \left\{ \tan\left(\arcsin\left(\frac{\lambda_1}{d}\right)\right) - \tan\left(\arcsin\left(\frac{\lambda_2}{d}\right)\right) \right\} + M\Delta S \leq$$

$$A_{min} \leq L \times \tan\left(\arcsin\left(\frac{\lambda_1}{d}\right)\right)$$

The above-mentioned is a measure for the problem of the emission point shift on the detection plane of the photodiode, however, a spot position of a first wavelength and a spot position of a second wavelength respectively formed in the sample by the objective lens 123 are also displaced in a direction perpendicular to an optical axis of the objective lens because of the emission point shift ΔS of the 2-wavelength semiconductor laser. Then, in this embodiment, the quantity of a focal point shift on the sample caused by the quantity of the emission point shift of the 2-wavelength semiconductor laser is stored in a memory module 142 in a signal processing unit 105 beforehand, a pair of two detection signals is selected referring to the quantity of the focal point shift so that a detection signal by the first wavelength and a detection signal by the second wavelength become detection signals in the same light spot position, and the ratio of the detection signals for the two wavelengths is operated. Therefore, it is desirable that displacement in the direction perpendicular to the optical axis of the objective lens 123 by an actuator 122 is set to integral times or 1/an integer and others of the quantity of the focal point shift on the sample.

Third Embodiment

Figure 11:
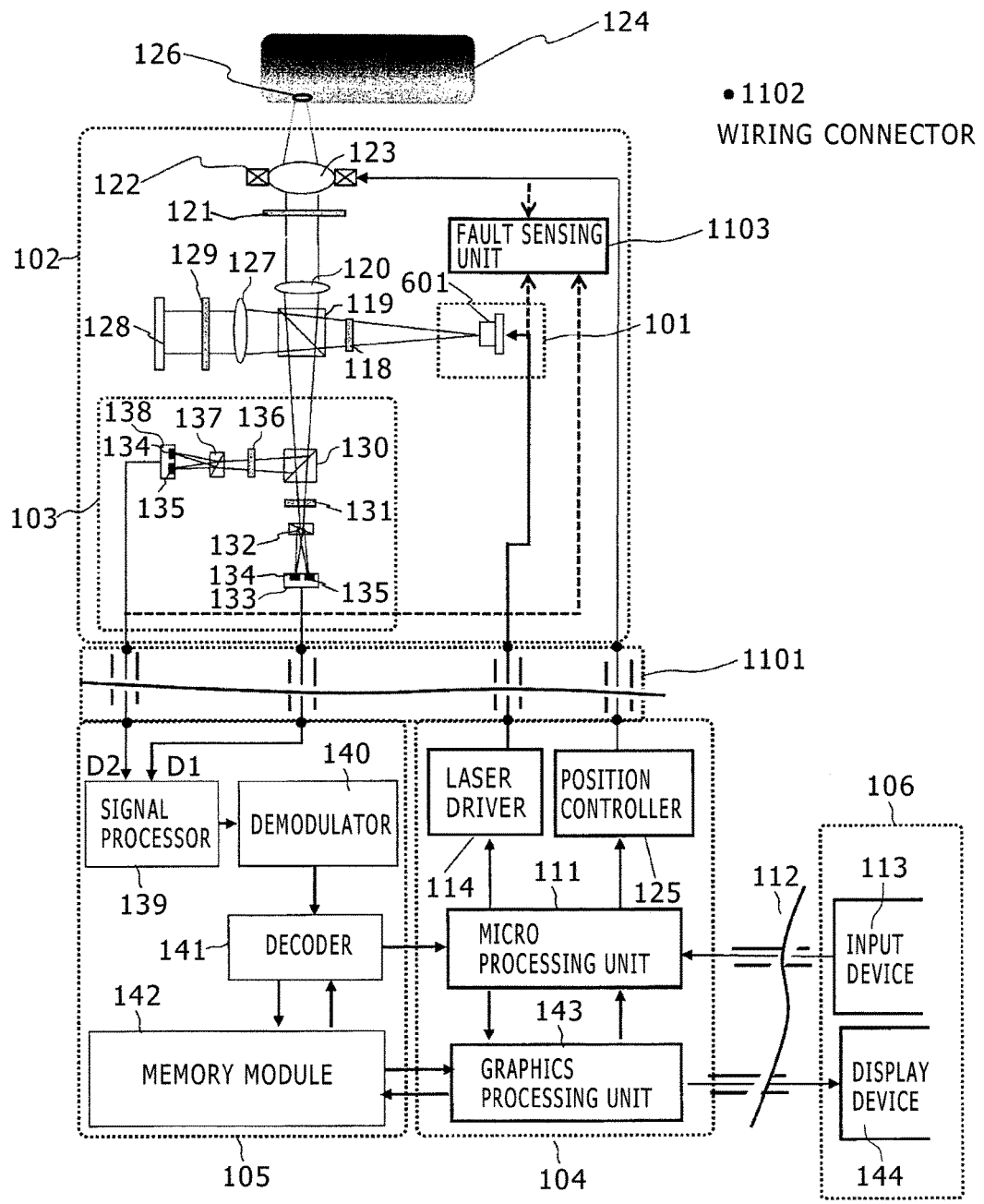
FIG. 11 is a block diagram showing an optical tomograph equivalent to a third embodiment of the present invention.

FIG. 11 is a block diagram showing an optical tomograph equivalent to a third embodiment of the present invention. In this embodiment, a layout of electric wiring is extended by integrating a light source unit 101, an optical imaging head unit 102 and a photodetection unit 103 as a module and electrically connecting a control unit 104 and a signal processing unit 105 to the module via a connecting unit 1101. Distance from the control unit 104 and the signal processing unit 105 to the optical imaging head unit 102, that is, distance to a measurement object can be changed by varying the length of the electric wiring, and an analyzer configured by the control unit 104 and the signal processing unit 105 and an examination instrument integrated as the module can be separated. A wiring connector 1102 is added to any of the light source unit 101, the optical imaging head unit 102, the photodetection unit 103, the control unit 104 and the signal processing unit 105 in accordance with this change. Further, a fault sensing unit 1103 is added to the optical imaging head unit 102 in the module. The fault sensing unit 1103 is electrically connected to the light source unit 101, the optical imaging head unit 102 and the photodetection unit 103.

The fault sensing unit 1103 and the light source unit 101 are electrically connected via a back monitoring photodetector provided to a 2-wavelength semiconductor laser 601. The back monitoring photodetector is packaged in a general semiconductor laser module and is used for measuring the output power of the semiconductor laser. For example, such control that desired output power is acquired by adjusting the volume of current from a laser driver to keep a back monitoring signal at fixed intensity even if an environmental condition varies is performed. That is, it is enabled by checking a signal from the back monitoring photodetector to judge whether the replacement of the semiconductor laser easily damaged by deterioration by heat history and a fault by an electric factor, that is, the light source unit 101 is required or not.

The fault sensing unit 1103 and the optical imaging head unit 102 are electrically connected via an actuator 122. The actuator 122 is used for scanning an objective lens by supplying electricity to a coil as described above, physical deterioration (abrasion) and others are not only readily caused because of scanning, that is, mechanical driving but when current exceeding assumption is applied to the coil, a fault such as wiring is cut by Joule heat and others in an electric circuit in the actuator and the objective lens cannot be scanned may be caused. Then, it can be discriminated by checking current applied to the actuator 122 whether the above-mentioned fault is caused or not.

The fault sensing unit 1103 and the photodetection unit 103 are electrically connected via photodiodes 134, 135. The photodiodes 134, 135 are also readily damaged by deterioration by heat history and a fault by an electric factor like the semiconductor laser, however, in addition, in an optical interferometer in the present invention, even in a case that the photodiode itself is not damaged, no desired optical interference signal is acquired by the displacement of an optical part such as a lens, a prism, a polarizing plate and a photodiode in the optical imaging head unit 102 and the photodetection unit 103. Such displacement is often caused by the repetition of a temperature change and physical impact such as a fall and a crash. Then, it can be discriminated by checking whether desired optical interference signal intensity is acquired based upon output voltage from the photodiodes 134, 135 or not when the tomograph according to the present invention is activated whether the above-mentioned fault is caused or not.

The fault sensing unit 1103 is configured by a discriminating circuit for discriminating the fault, a display for declaring the unit in which a fault occurs and further, a battery for enabling self-driving even if no driving power is supplied from the tomograph.

Figure 12:
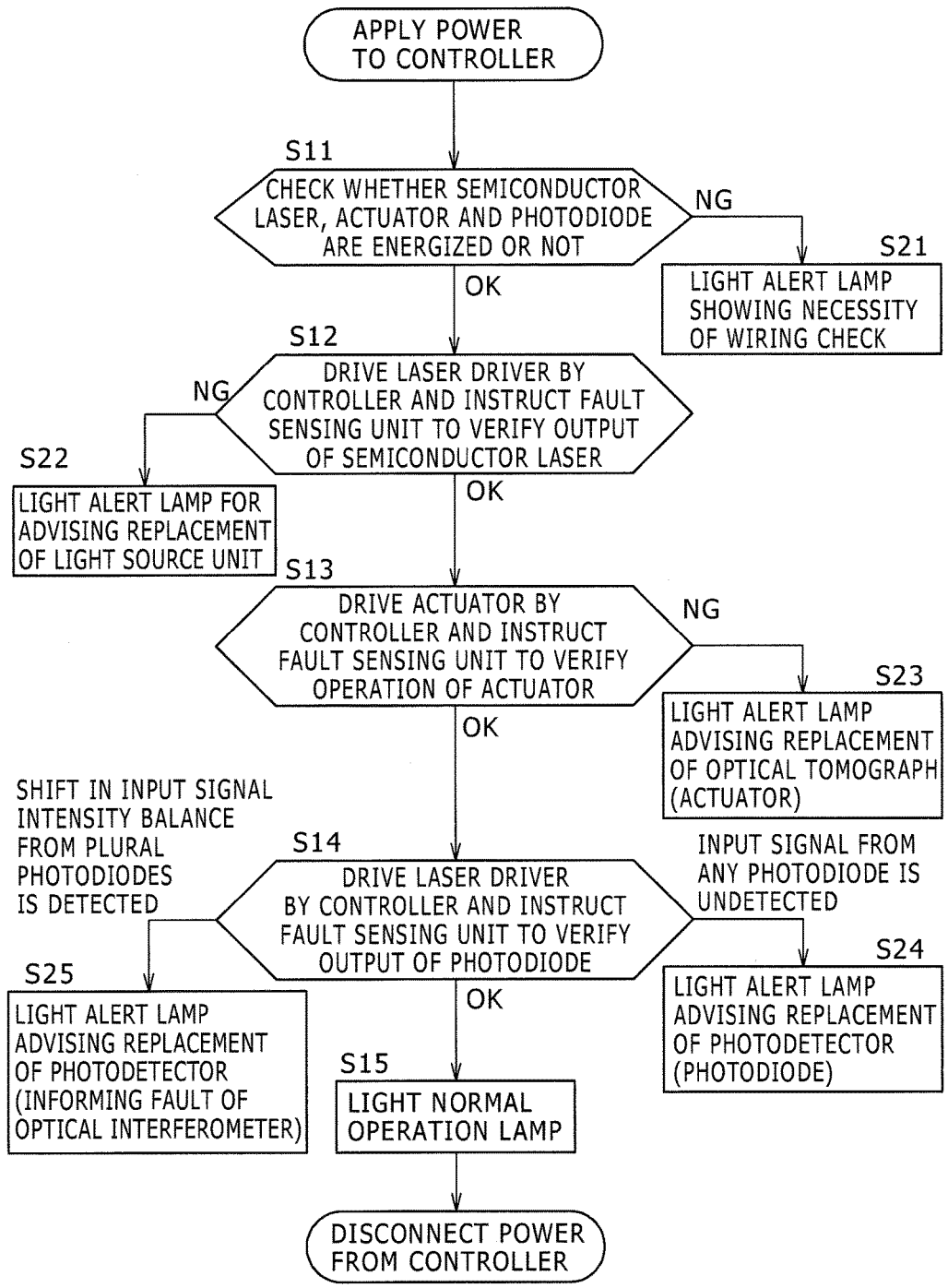
FIG. 12 is a flowchart showing the operation of a fault sensing unit.

The other basic configuration and the other operation are the same as those in the first and second embodiments. Referring to FIG. 12, a procedure for discriminating a fault by the fault sensing unit in this embodiment will be described below. After power is applied to the control unit 104, processing proceeds to a step 11 and the fault sensing unit checks whether the semiconductor laser 601, the actuator 122 and the photodiodes 134, 135 are energized or not. At this time, when the fault sensing unit senses abnormality, the processing proceeds to a step 21 and the fault sensing unit 1103 lights an alert lamp for informing about the necessity of a wiring check on its display. If no abnormality is sensed in the step 11, the processing proceeds to a step 12, the laser driver 114 is driven by the control unit 104, and the fault sensing unit 1103 verifies the output of the semiconductor laser based upon the output of the back monitoring photodetector of the 2-wavelength semiconductor laser 601. At this time, if abnormality is sensed, the processing proceeds to a step 22 and the fault sensing unit 1103 lights an alert lamp for advising the replacement of the light source unit on its display. When no abnormality is sensed in the step 12, the processing proceeds to a step 13, the actuator 122 is driven by the control unit 104, and in the fault sensing unit 1103, and current that flows into the actuator is monitored so as to verify the operation of the actuator. When abnormality is sensed, the processing proceeds to a step 23 and the fault sensing unit 1103 lights an alert lamp for advising the replacement of the optical tomograph (the actuator) on its display.

If no abnormality is sensed in the step 13, the processing proceeds to a step 14, the laser driver 114 is driven by the control unit 104, and the fault sensing unit 1103 verifies the output of the photodiodes 134, 135. At this time, if an input signal from either photodiode is undetected, the processing proceeds to a step 24 and the fault sensing unit 1103 lights an alert lamp for advising the replacement of the photodetection unit (the photodiode) on its display. Besides, when the breakdown of a balance in intensity of input signals from the plural photodiodes is detected, the processing proceeds to a step 25 and the fault sensing unit 1103 lights an alert lamp for advising the replacement of the photodetection unit (for informing about a fault of an optical interferometer) on its display.

In this embodiment, the light source unit 101, the optical imaging head unit 102 and the photodetection unit 103 respectively integrated as the module which are susceptible to mechanical vibration and a thermal effect as the optical interferometer can be collectively replaced by executing a fault discrimination flow shown in FIG. 12, and high maintainability can be realized.

Fourth Embodiment

Figure 13:
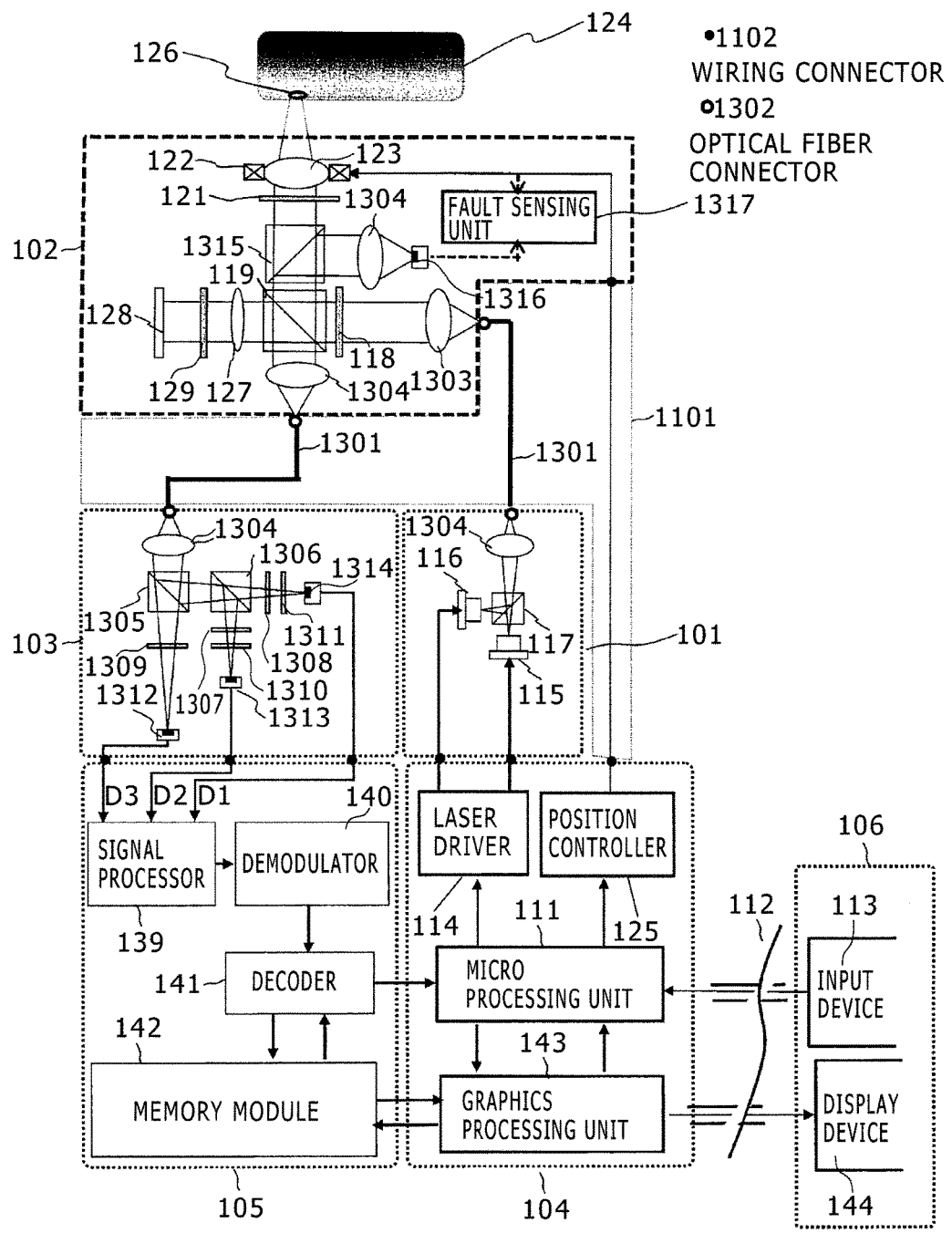
FIG. 13 is a block diagram showing an optical tomograph equivalent to a fourth embodiment of the present invention.

FIG. 13 is a block diagram showing an optical tomograph equivalent to a fourth embodiment of the present invention. In this embodiment, only an optical imaging head unit 102 can be used with it separated from a body of the tomograph by providing not only electric wiring as in the third embodiment but an optical fiber 1301 in addition to a connecting unit 1101. Further lightening is promoted by making only the optical imaging head unit 102 a unit and the similar usage to the existing fiber scope can be realized. In accordance with this change, an optical fiber connector 1302 is added to any of the light source unit 101, the optical imaging head unit 102 and the photodetection unit 103. Further, the similar function of an optical system to the functions in the first to third embodiments is realized by installing a collimating lens 1303 and a condenser 1304 before and after the optical fiber connector 1302.

Further, in this embodiment, the configuration of the photodetection unit 103 is changed and simple configuration that the number is reduced from the four photodetectors in the first to third embodiments to three photodetectors is adopted. In the photodetection unit 103, an incident luminous flux is split in three by unpolarized beam splitters 1305, 1306, one luminous flux of them is made to pass a phase plate 1307 that makes s-polarized light have phase difference of 120 degrees with p-polarized light, another luminous flux is made to pass a phase plate 1308 that makes s-polarized light have phase difference of 240 degrees with p-polarized light, three luminous fluxes are all transmitted in polarizers 1309, 1310, 1311 that transmit only light polarized by degrees, and the three luminous fluxes are detected by photodetectors 1312, 1313, 1314. The outputs of these photodetectors are expressed in the following expressions (20), (21), (22). In this case, integration is the one for a component in an electric field.

[Mathematical expression 15]

$$I_1 = \int_{-\infty}^{\infty}\int_{-\infty}^{\infty} \left| \frac{1}{\sqrt{3}} E_s + \frac{1}{\sqrt{3}} E_r \right|^2 dxdy \qquad (20)$$

$$= \frac{1}{3}\int_{-\infty}^{\infty}\int_{-\infty}^{\infty} (|E_s|^2 + |E_r|^2) dxdy + \frac{1}{3}\int_{-\infty}^{\infty}\int_{-\infty}^{\infty} E_r^* E_s dxdy + C.C.$$

$$I_2 = \int_{-\infty}^{\infty}\int_{-\infty}^{\infty} \left| \frac{1}{\sqrt{3}} E_s + \frac{1}{\sqrt{3}} e^{i\pi/3} E_r \right|^2 dxdy \qquad (21)$$

$$= \frac{1}{3}\int_{-\infty}^{\infty}\int_{-\infty}^{\infty} (|E_s|^2 + |E_r|^2) dxdy + \frac{1}{3}\int_{-\infty}^{\infty}\int_{-\infty}^{\infty} e^{i\pi/3} E_r^* E_s dxdy + C.C.$$

-continued $$I_3 = \int_{-\infty}^{\infty}\int_{-\infty}^{\infty}\left|\frac{1}{\sqrt{3}}E_s + \frac{1}{\sqrt{3}}e^{i2\pi/3}E_r\right|^2 dxdy \quad (22)$$

$$= \frac{1}{3}\int_{-\infty}^{\infty}\int_{-\infty}^{\infty}(|E_s|^2 + |E_r|^2)dxdy + \frac{1}{3}\int_{-\infty}^{\infty}\int_{-\infty}^{\infty}e^{i2\pi/3}E_r^*E_s dxdy + C.C.$$

Operation expressed in an expression (23) is executed based upon these outputs and output equivalent to an expression (24) is acquired based upon these.

[Mathematical expression 16]

$$\left(\int_{-\infty}^{\infty}\int_{-\infty}^{\infty}|E_sE_r|dxdy\right)^2 = \left(\frac{\sqrt{3}(-2I_1+3I_2-I_3)}{2}\right)^2 + \left(\frac{3(I_2-I_3)}{2}\right)^2 \quad (23)$$

$$D_1^2 + D_2^2 = \left(\int_{-\infty}^{\infty}\int_{-\infty}^{\infty}|E_rE_{s1}|dxdy\cos\phi\right)^2 + \quad (24)$$

$$\left(\int_{-\infty}^{\infty}\int_{-\infty}^{\infty}|E_rE_{s1}|dxdy\sin\phi\right)^2$$

$$= \left(\int_{-\infty}^{\infty}\int_{-\infty}^{\infty}|E_rE_{s1}|dxdy\right)^2$$

The expression (24) shows that the above-mentioned interference light can acquire the similar signal light intensity to that in the case of interference light of four different phases. In this embodiment, the example that the intensity of interference light of three different phases is detected is described, however, signal light intensity can be also acquired by detecting the intensity of interference light of plural three, four or five phases by adjusting the phases and polarization.

Further, in the optical imaging head unit 102, a part of measured light is split by adding a polarized beam splitter 1315 and is focused on the photodiode 1316 using the condenser 1304. The polarized beam splitter 1315 is designed in view of luminous energy required for optical tomography so that the spectral ratio of transmitted light and reflected light is 95:5 and extracted light is minimized. In the photodiode 1316, a voltage signal equivalent to detected light power is generated and as in the third embodiment, the photodiode is electrically connected to the fault sensing unit 1317. Besides, an actuator 122 is also electrically connected to the fault sensing unit 1317 as in the third embodiment. In addition, a signal that drives the actuator 122 is supplied via wiring of the connecting unit 1101 that connects the wiring connector of the control unit 104 and the wiring connector of the optical imaging head unit 102, and the fault sensing unit 1317 senses a fault of the actuator by monitoring the driving signal.

In the meantime, as the light source unit 101 and the photodetection unit 103 are arranged in the vicinity of a control unit 104 and a signal processing unit 105, the detection of a fault of these units is performed by the control unit 104 as in a general machine.

Figure 14:
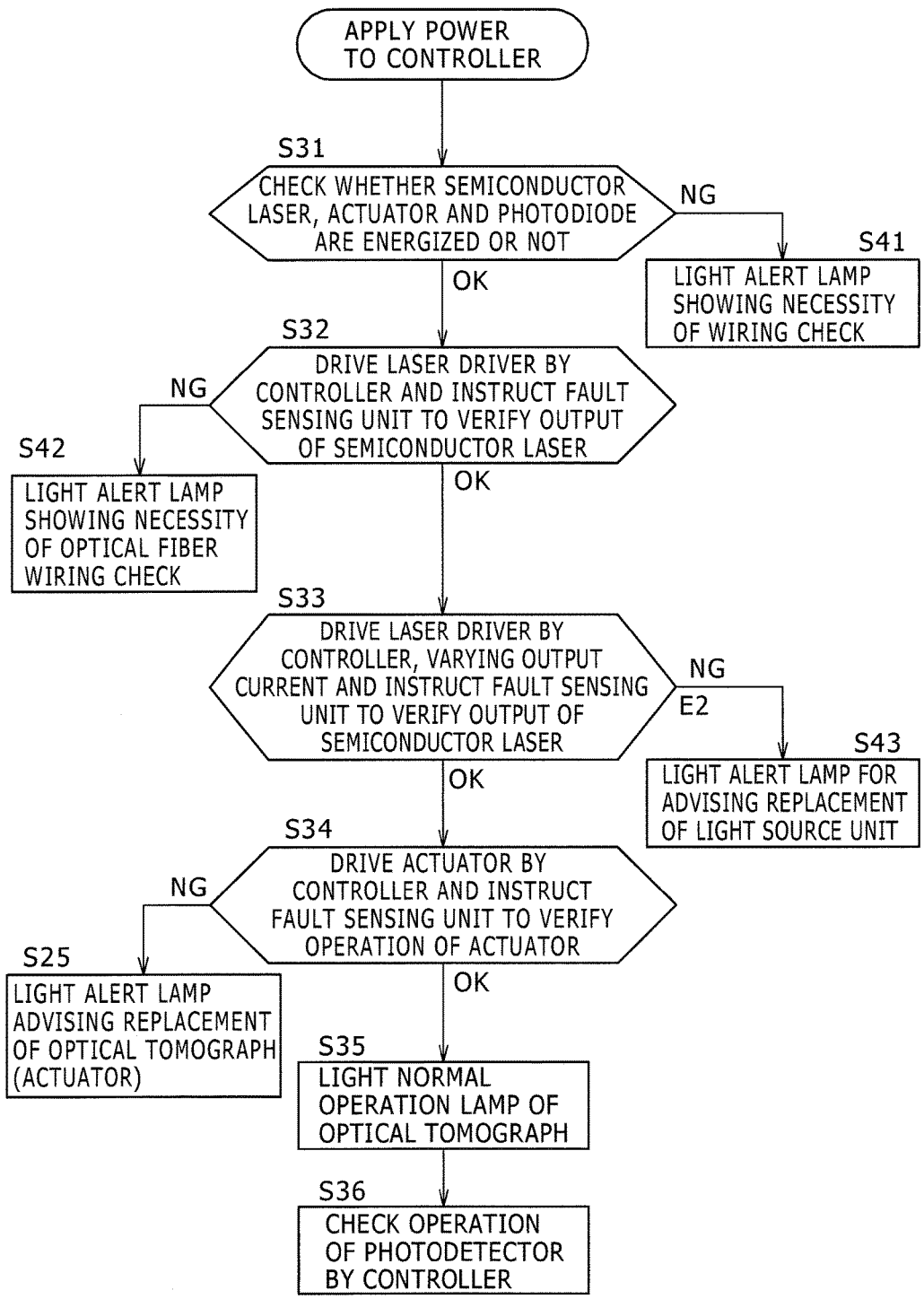
FIG. 14 is a flowchart showing the operation of a fault sensing unit.

Referring to FIG. 14, a procedure for discriminating a fault by a fault sensing unit in this embodiment will be described below. After power is applied to the control unit 104, processing proceeds to a step 31 and the fault sensing unit checks whether semiconductor lasers, an actuator 122 and a photodiode 1316 are energized or not. At this time, if abnormality is detected, the processing proceeds to a step 41 and the fault sensing unit 1317 lights an alert lamp for informing about the necessity of a wiring check on its display. When no abnormality is detected in the step 31, the processing proceeds to a step 32, a laser driver 114 is driven by the control unit 104, the fault sensing unit 1317 monitors a signal from the photodiode 1316, and the fault sensing unit verifies the outputs of the semiconductor lasers 115, 116. If abnormality is detected, the processing proceeds to a step 42 and the fault sensing unit 1317 lights an alert lamp for informing about the necessity of an optical fiber wiring check on its display.

When no abnormality is detected in the step 32, the processing proceeds to a step 33, the laser driver 114 is driven by the control unit 104, varying output current, the fault sensing unit 1317 monitors a signal from the photodiode 1316, and the fault sensing unit verifies the outputs of the semiconductor lasers 115, 116. If abnormality is detected, the processing proceeds to a step 43 and the fault sensing unit 1317 lights an alert lamp for advising the replacement of the light source unit on its display. When no abnormality is detected in the step 33, the processing proceeds to a step 34, the actuator 122 is driven by the control unit 104, and the fault sensing unit verifies the operation of the actuator. If abnormality is detected, the processing proceeds to a step 44 and the fault sensing unit 1317 lights an alert lamp for advising the replacement of the optical tomograph (the actuator) on its display.

When no abnormality is detected in the step 34, the processing proceeds to a step 35 and a lamp for showing that the optical tomograph is normally operated is lit. The processing proceeds to a step 36 and the control unit checks the operation of the photodetection unit.

The other basic configuration and the other operation in this embodiment are the same as those in the first, second and third embodiments. In this embodiment, the optical imaging head unit 102 as a module which is susceptible to mechanical vibration and a thermal effect as an optical interferometer can be collectively replaced by performing a fault discriminating flow shown in FIG. 14 and high maintainability can be realized.

The present invention is not limited to the above-mentioned embodiments and various variations are included. For example, the embodiments are detailed description for plainly explaining the present invention and the present invention is not necessarily limited to the embodiments provided with the described all configurations. Besides, a part of the configuration of the certain embodiment can be replaced with the configuration of another embodiment and in addition, the configuration of another embodiment can be added to the configuration of the certain embodiment. Further, another configuration can be added to a part of the configuration of each embodiment and a part of the configuration of each embodiment can be deleted and replaced.

According to the present invention, the tomograph that can output a stable amplified signal without being influenced by various variation of characteristics caused in an actual optical system, performs interference-type optical tomography by the method different from OCT and at the same time, displays the distribution in a tomographic direction of an examination object substance in view of spectral characteristics of the examination object substance can be provided.

What is claimed is:

1. An optical tomograph, comprising:
   a light source;
   an optical imaging head unit;
   a photodetection unit;
   a controller;
   a signal processor;
   an input device; and
   a display device;

wherein the light source radiates laser light centered around different single wavelengths;

wherein the optical imaging head unit includes a first optical element that splits a luminous flux including the laser light of different wavelengths outgoing from the light source into first and second luminous fluxes, an objective lens that focuses the first luminous flux on a sample, irradiates the sample and receives reflected light reflected from the sample as signal light, a reflector that reflects the second luminous flux as reference light without radiating the second luminous flux toward the sample, a second optical element that multiplexes the signal light and the reference light and an actuator that drives the objective lens at least in a direction of an optical axis during a measurement of a scanning operation, wherein the reflected light is generated at a depth of the optical axis;

wherein the photodetection unit includes a plurality of photodetectors and an interference optical system that generates three or more coherence beams differing in phasic relationship from one another and from multiplexed light of the signal light and the reference light on each photodetector, and wherein the photodetection unit further includes a diffraction grating, a phase plate disposed downstream from the diffraction grating, a λ/2 plate disposed downstream from the phase plate, and a Wollaston prism, wherein the phase plate is inclined such that a phase difference of π/2 is made between passing luminous fluxes, and wherein the λ/2 plate is inclined by 45 degrees;

wherein the controller controls the actuator and a luminescent state of the laser light of different wavelengths;

wherein the signal processor acquires a distribution of a substance on a section of an object in the sample by using the outputs of the plurality of photodetectors for every input wavelength, acquiring a detection signal at each input wavelength and calculating the ratio of intensities of detection signals at the different wavelengths for every position in the sample; and wherein the input device is configured to input a position to be observed in the sample to the optical imaging head unit and the display device displays the distribution on the section of the object of examination.

2. The optical tomograph according to claim 1, wherein:
the light source includes at least two laser elements for radiating light of different wavelengths and an optical element that multiplexes luminous fluxes from at least the two laser elements; and
the objective lens corresponds to the different wavelengths.

3. The optical tomograph according to claim 1, wherein:
the light source includes a 2-wavelength semiconductor laser having first and second semiconductor chips that can selectively radiate light of two wavelengths;
the photodetection unit includes four photodetectors;
and the interference optical system includes a diffraction grating for leading a luminous flux onto the four photodetectors.

4. The optical tomograph according to claim 3, wherein:
when wavelengths of the 2-wavelength semiconductor laser are λ1, λ2 (λ1 >λ2), the quantity of a shift of an emission point on plane perpendicular to a direction at which light is emitted from the 2-wavelength semiconductor laser is ΔS, the pitch of the diffraction grating is d, distance from the diffraction grating to detection planes of the four photodetectors is L, the imaging magnification of an emission point plane and the detection plane of the 2-wavelength semiconductor laser is M and the size of the largest photodetector of the four photodetectors is A, A meets the following expression.

[Mathematical expression 1]

$$L \times \left\{\tan\left(\arcsin\left(\frac{\lambda_1}{d}\right)\right) - \tan\left(\arcsin\left(\frac{\lambda_2}{d}\right)\right)\right\} + M\Delta S \le$$

$$A_{min} \le L \times \tan\left(\arcsin\left(\frac{\lambda_1}{d}\right)\right)$$

5. The optical tomograph according to claim 3,
wherein the signal processor includes a memory module that stores a quantity of a shift of a focal point on the sample accompanied by the quantity of the shift of the emission point of the 2-wavelength semiconductor laser, and
wherein the signal processor selects so that a detection signal acquired in a position in a direction perpendicular to an optical axis of the objective lens is in the same position as a detection signal at the two wavelengths, the signal processor using the quantity of the shift of the focal point extracted from the memory module and the calculated ratio of intensities of detection signals at the two wavelengths.

6. The optical tomograph according to claim 1,
wherein the light source, the optical imaging head unit, the photodetection unit, the controller and the signal processor are provided with a connector, and
wherein the light source, the optical imaging head unit and the photodetection unit are electrically connected to the controller and the signal processor via a connecting unit and the connector respectively including wiring.

7. The optical tomograph according to claim 1,
wherein the light source, the optical imaging head unit and the photodetection unit are provided with a wiring connector and an optical fiber connector,
wherein the controller and the signal processor are provided with the wiring connector,
wherein the light source, the optical imaging head unit and the photodetection unit are electrically connected to the controller and the signal processor via a connecting unit and the wiring connector respectively including wiring, and
wherein the optical imaging head unit is optically connected to the light source and the photodetection unit via a connecting unit and the optical fiber connector respectively including an optical fiber.

8. The optical tomograph according to claim 1,
wherein the laser light of the plurality of wavelengths is radiated onto the sample in time division.

9. The optical tomograph according to claim 1, comprising:
four photodetectors,
wherein interference phases on the four photodetectors differ by integral multiples of substantially 90 degrees; and
wherein the sum of the square of a first differential signal between two of the photodetectors having interference phases that differ by substantially 180 degrees and the square of a second differential signal from the residual two photodetectors is equal to the detection signal.

10. The optical tomograph according to claim 1, comprising:
three photodetectors,
wherein interference phases on the three photodetectors are mutually different by integral times of 120 degrees; and
wherein signals from the three photodetectors are operated in a quadratic polynomial and the detection signal is acquired.

11. An optical imaging head unit, comprising:
a first optical fiber connector;
a second optical fiber connector;
a wiring connector;
a collimating lens that makes laser light centered around a single wavelength led from the first optical fiber connector parallel luminous fluxes;
a first optical element that splits the luminous flux that passes the collimating lens into first and second luminous fluxes;
an objective lens that focuses the first luminous flux on a sample, irradiates the sample and receives reflected light reflected from the sample as signal light;
an actuator that drives the objective lens at least in a direction of an optical axis during a measurement of a scanning operation, wherein the reflected light is generated at a depth of the optical axis;
a reflector that reflects the second luminous flux as reference light without radiating the second luminous flux onto the sample;
a second optical element that multiplexes the signal light and the reference light;
a diffraction grating which demultiplexes the signal light and the reference light
a phase plate disposed downstream from the diffraction grating, wherein the phase plate is inclined such that a phase difference of $\pi/2$ is made between passing luminous fluxes;
a $\lambda/2$ plate disposed downstream from the phase plate, wherein the $\lambda/2$ plate is inclined by 45 degrees;
a Wollaston prism;
a condenser that converges the luminous flux multiplexed by the second optical element on the second optical fiber connector; and
wiring that transmits an actuator driving signal input from the wiring connector to the actuator.

12. The optical imaging head unit according to claim 11, further comprising:
a third optical element which is arranged on an optical path of the first luminous flux and extracts a part of the first luminous flux;
a photodetector that detects the luminous flux extracted by the third optical element; and
a fault sensing unit that monitors the output of the photodetector and the actuator driving signal and detects a fault.

13. An optical tomographic method, comprising:
splitting a luminous flux including laser light centered around a plurality of single wavelengths different in optical sensitivity for material to be examined into first and second luminous fluxes;
driving, by an actuator, an objective lens at least in a direction of an optical axis during a measurement of a scanning operation;
focusing, by the objective lens, the first luminous flux on a sample and irradiating the sample;
leading light reflected from the sample to a plurality of photodetectors of a photodetection unit, wherein the reflected signal light is generated at a depth of the optical axis,. wherein the photodetection unit further includes a diffraction grating, a phase plate disposed downstream from the diffraction grating, a $\lambda/2$ plate disposed downstream from the phase plate, and a Wollaston prism, wherein the phase plate is inclined such that a phase difference of $\pi/2$ is made between passing luminous fluxes, and wherein the $\lambda/2$ plate is inclined by 45 degrees;
leading the second luminous flux to the plurality of photodetectors as reference light without radiating the second luminous flux onto the sample;
rotating the first luminous flux and the second luminous flux by the $\lambda/2$ plate;
making the signal light and the reference light optically interfere on the plurality of photodetectors in a state in which both are mutually different in optical phase relation;
operating using the outputs of the plurality of photodetectors wavelengths;
for input for each of the plurality of acquiring a result of the operation as a detection signal that reflects internal structure of the sample at a focal point of the first luminous flux;
operating the ratio in intensity of the detection signals at each wavelength at the same focal point in the sample; and
visualizing the distribution of the object in an optical axis direction in the sample by acquiring the detection signal, varying a focused position luminous flux in the sample so as to enable observing a section of the sample.

* * * * *